US00PP11894P2

(12) United States Plant Patent
Kent

(10) Patent No.: US PP11,894 P2
(45) Date of Patent: May 29, 2001

(54) GUZMANIA PLANT NAMED 'GUZ 222'

(75) Inventor: Jeffrey C. Kent, Vista, CA (US)

(73) Assignee: Kent's Bromeliad Nursery, Inc., Vista, CA (US)

( * ) Notice: Subject to any disclaimer, the term of this patent is extended or adjusted under 35 U.S.C. 154(b) by 0 days.

(21) Appl. No.: 09/248,491

(22) Filed: Feb. 9, 1999

(51) Int. Cl.[7] ..... A01H 5/00
(52) U.S. Cl. ..... Plt./371
(58) Field of Search ..... Plt./371

(56) References Cited

U.S. PATENT DOCUMENTS

P.P. 7,471 * 3/1991 Bak et al. ..... Plt./371
P.P. 9,922 * 6/1997 Rabin ..... Plt./371

* cited by examiner

*Primary Examiner*—Bruce R. Campell
*Assistant Examiner*—Kent L. Bell
(74) *Attorney, Agent, or Firm*—James A. Lucas; Driggs, Lucas, Brubaker & Hogg Co., L.P.A.

(57) ABSTRACT

A new cultivar of Guzmania named 'Guz 222' characterized by a plant form that is vase shaped; plant height of about 22–24 inches and leaves measuring 16¾ inches in length and 2½ inches in width.

1 Drawing Sheet

BACKGROUND OF THE INVENTION

The present invention relates to a newly developed interspecific hybrid Guzmania plant resulting from a planned breeding program that I conduct on an ongoing basis. The objects of the breeding program include the crossing of selected parent plants from the numerous, compatible species within the genus, to obtain plants with novel and attractive phenotypes, coloration, and flowering forms. Other important selection factors may include ultimate plant size and shape, disease resistance, tolerance to different soil and growing conditions and vigor.

Among the objects of my program are to produce plants of the Bromeliaceae family which will be attractive to the consumer; which will develop reasonably rapidly under controlled conditions; and, which will retain for a long term, highly attractive and bright inflorescence; i.e., bract coloration, after being induced into the flowering stage. It is a specific object to provide a low maintenance plant which will be a long term decorative appointment offering an exotic color splash in the home of a buyer, or to serve as a substitute for flowering plants which have a shorter flowering duration in, for example, indoor plant and flower scapes. Finally, it is an object to develop plants which may be easily and efficiently multiplied by state-of-the-art tissue culture methods while continuing the distinctive characteristics of the plants through progressive clonal generations.

The plant of this disclosure was a seedling of a crossing between the unpatented seed parent *Guzmania lingulata* 'Equador' and the unpatented pollen parent *Guzmania wittmackii* 'Red Orange Equador'. With the recognition that this seedling satisfied the objects of the breeding program, the individual was isolated and set aside for further observation and testing. The resulting selection has been assigned the designation 'GUZ 222' for purposes of identification. This plant has been reproduced by division at Vista Calif., and the clonal specimens resulting therefrom have been determined to be identical to the original selection in all distinguishing characteristics. The superior attributes of this plant will be revealed in the botanical descriptions to follow.

SUMMARY OF THE INVENTION

The distinguishing characteristics of 'GUZ 222' are described as follows: This Bromeliad is a sterile $F_1$ hybrid which flowers about 15 months following the first transplanting of a ½" plant. It forms an ovate, somewhat undulate scape bract, and leaves elliptical in shape with a truncate base. The scape bracts have a bright red coloration that extends the length of the scape. The color is unusual when compared with the color of the scape bracts of other hybrids known to me which tend toward orange-red or red-purple. The scape bracts are comparatively widely spaced, similar to those of the pollen parent. The white tips of the floral bracts are well excerted above the scape bracts, contributing to the distinctiveness of the hybrid. The plant remains in bright color for up to 2 months under low interior light conditions.

Plants of the new Guzmania can be compared to plants of the Guzmania cultivars 'Equador' and 'Red Orange Equador'. In side-by-side comparisons conducted in Vista, Calif., plants of the new Guzmania differ from plants of 'Equador' primarily in leaf, scape bract, and floral bract coloration. Plants of the new cultivar are larger in size than plants of 'Equador'. Plants of the new Guzmania differ from plants of 'Red Orange Equador' primarily in scape bract and floral bract coloration. Plants of the new cultivar are smaller in size than plants of 'Red Orange Equador'.

BRIEF DESCRIPTION OF THE DRAWING

The single color photograph depicts a mature specimen of the plant in mid to late flowering stage. Illustrated are the mature leaves, scape bracts and floral bracts. The color definitions in the specification have been taken from the R.H.S. Colour Chart of The Royal Horticultural Society. While the colors depicted are believed to be of a high level of color fidelity, the coloration of this plant should be understood to be approximate, and somewhat variable as a function of cultural conditions and horticultural practices. For example, the bract color might slightly fade if the plant is subjected to bright light and the leaf color may vary depending on the composition and the concentration of fertilizer that may be applied to the plant.

BOTANICAL DESCRIPTION OF THE PLANT

General characteristics:

*Type.*—Monocot perennial.

*Habit.*—Moderately vigorous growing from initial transplant of a ½" plant to anthesis in approximately 66 weeks in coastal south California, upright, spreading and dense.

*Hardiness.*—Tender. Leaves will be damaged at temperatures below 32° F.; buds are destroyed at temperatures below 32° F.; entire plant will not survive exposure to temperatures below 32° F. for several hours.

*Size.*—About 22–24 inches in width and about 22–24 inches in height, including Inflorescence.

*Shape.*—Vase formed.

Leaves: Medium size; Length— 16¾ inches; Width— 2½ inches at base; margins smooth. Tips acuminate, medium thickness, dark green 147A and smooth; arching upper leaves recurved downward at tips, truncate at base; color— 47-B on adaxial and abaxial, lined at base 46A in color blending into solid 46-A, ½ the length of leaf, remaining portion is 147A, adaxial and abaxial; lower leaves acutely pointed, upper leaves abruptly pointed; apetiolate.

Inflorescence: A branched spike.

Scape bracts: Acutely pointed, ovate, 5¼"×2¼" to 2½"×1⅞" at apex, tips recurved downward, colored adaxial and abaxial 147-A at base with lineation 45-B in color ¼ of distance to apex blending into solid 45-B. Some bracts undulate; upper scape bracts 149-A at base blending into 45-B.

Floral bracts: 2½"×⅝", color adaxial and abaxial 147-A at base, some staining with 45-B acutely pointed; the apex of some upper floral bracts appear white when viewed under artificial light, bracts ovate in shape, base truncate.

Asexual reproduction:

*Method.*—Division.

*Location.*—Vista, Calif.

Floral buds:

*Shape.*—Pear shaped.

*Length.*—2¼" to 2½".

*Width.*—½" to 1".

*Color.*—150-B.

Flowers: Flowers without apedicel, barely open at anthesis, large.

*Corolla.*—Cylindrical.

*Three sepals.*—1¼"×¼" translucent, 2B in color (adaxial and abaxial sides).

*Three petals.*—2⅛"×5/16" 2-B in color (adaxial and abaxial sides), joined 1½" from base.

Fruit seed: None produced.

Reproductive organs: Typical for genus and species.

*Ovaries.*—superior, three locules ½" long by ¼" wide, 150-D in color.

*Pistils.*—1 present.

*Style.*—2" long by ¼" wide, 150-D in color.

*Stamens.*—6 present.

*Filament.*—1½" long.

*Anthers.*—3/16" long, 7-D in color. Pollen not produced.

Disease and pest resistance: This variety has resistance to plant diseases and pests comparable to that of other variegated Guzmania cultivars.

What is claimed is:

1. A new and distinct variety of Guzmania plant named 'Guz 222' as illustrated and described.

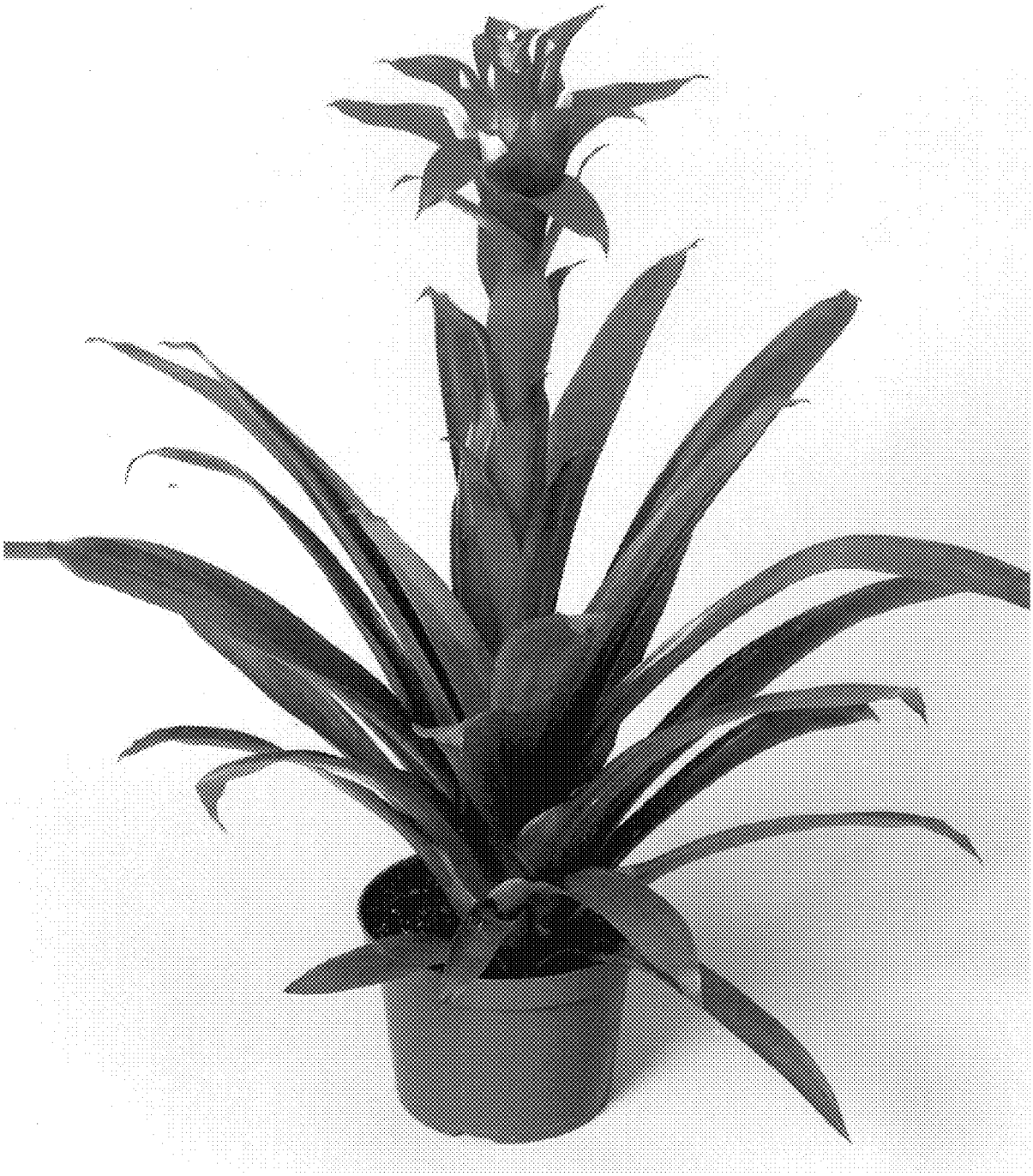

* * * * *